(12) United States Patent
McMillan et al.

(10) Patent No.: US 10,099,358 B2
(45) Date of Patent: Oct. 16, 2018

(54) GRIPPING TOOL

(71) Applicant: Enztec Limited, Christchurch (NZ)

(72) Inventors: Iain Alexander McMillan, Christchurch (NZ); Simon John Faichen Davis, Christchurch (NZ)

(73) Assignee: Enztec Limited, Christchurch (NZ)

( * ) Notice: Subject to any disclaimer, the term of this patent is extended or adjusted under 35 U.S.C. 154(b) by 323 days.

(21) Appl. No.: 15/004,482

(22) Filed: Jan. 22, 2016

(65) Prior Publication Data

US 2016/0213389 A1 Jul. 28, 2016

(51) Int. Cl.
| | | |
|---|---|---|
| *A61B 17/00* | (2006.01) | |
| *A61B 17/58* | (2006.01) | |
| *A61B 17/60* | (2006.01) | |
| *A61F 2/00* | (2006.01) | |
| *B25C 11/00* | (2006.01) | |
| *A61B 17/92* | (2006.01) | |

(52) U.S. Cl.
CPC .............. *B25C 11/00* (2013.01); *A61B 17/92* (2013.01)

(58) Field of Classification Search
CPC ................................ B25C 11/00; A61B 17/92
USPC ... 606/207, 104, 65, 208, 144–145, 147, 96, 606/205; 294/99.2, 15; 81/3.43–3.44, 81/64, 90.3; 254/18; 16/422; 30/120.1–120.3
See application file for complete search history.

(56) References Cited

U.S. PATENT DOCUMENTS

| | | | | |
|---|---|---|---|---|
| 4,227,730 A | * | 10/1980 | Alexander | A61B 17/122 294/131 |
| 4,248,233 A | * | 2/1981 | von Zeppelin | A61B 17/44 606/122 |
| 4,318,313 A | * | 3/1982 | Tartaglia | B25B 9/02 294/99.2 |
| 4,509,784 A | * | 4/1985 | Vollers | B67B 7/18 294/99.1 |
| 5,843,125 A | * | 12/1998 | Jempolsky | A61B 17/08 606/207 |
| 6,066,143 A | * | 5/2000 | Lane | A61B 17/92 606/104 |
| 7,189,243 B1 | * | 3/2007 | Seelig | A61B 17/92 606/104 |
| 7,506,908 B2 | * | 3/2009 | Metcalfe | B23B 51/12 294/99.2 |
| D768,855 S | * | 10/2016 | McMillan | D24/133 |
| D796,039 S | * | 8/2017 | McMillan | D24/133 |
| 9,750,554 B2 | * | 9/2017 | Lee | A61B 17/8872 |

(Continued)

*Primary Examiner* — Amy R Weisberg
(74) *Attorney, Agent, or Firm* — Richards Patent Law P.C.

(57) ABSTRACT

A gripping tool for extracting a pin during a surgical procedure, the gripping tool including: two lever arms, each arm having a nose end and a handle end, the two lever arms joined together proximate to but spaced apart from the nose end by a bridging portion, the bridging portion including a central fulcrum region; the nose ends of each the lever arms having one or more teeth adapted to interlock with the one or more teeth of the other lever arm; each nose end having a longitudinal aperture therein extending through the interlocking teeth adapted, in use, to align and receive the pin; such that in use, urging together the handle ends of the lever arms causes the nose ends to move relative to each other such that the interlocking teeth misalign and grip the pin.

19 Claims, 8 Drawing Sheets

(56) References Cited

U.S. PATENT DOCUMENTS

2010/0234851 A1* 9/2010 Graves ................... A61B 17/92
  606/104
2011/0000090 A1* 1/2011 Pau ......................... A47J 43/26
  30/120.2

* cited by examiner

GRIPPING TOOL

CROSS-REFERENCE TO RELATED APPLICATIONS

This invention incorporates by reference and claims priority to New Zealand App. No. 704136, filed on Jan. 23, 2015.

FIELD OF INVENTION

This invention relates to a gripping tool. More specifically, the invention relates to a gripping tool for use in gripping and extracting a pin during a surgical procedure.

BACKGROUND OF THE INVENTION

A range of pins are used in surgical procedures, particularly in the orthopaedic field. Pins are often used as markers to help facilitate alignment during a procedure, or to hold instruments such as cutting guides in place temporarily. Pins may be a range of sizes but often pins used in such procedures a very small and may not include a head portion which would otherwise make extraction easier.

Removal of such pins requires the body of the pin to be gripped strongly so that it can be successfully withdrawn from the substrate without breaking, and without the removal tool slipping from the pin. This is particularly difficult with pins of a very short length or which have short protrusions available to be gripped.

In a surgical environment easy of cleaning and sterilisation of instruments is also paramount. Instruments that can be quickly and easily cleaned between uses reduces surgery time and consequently improving patient outcomes.

A known pin removal tool is disclosed in WO2014/102541. The tool disclosed here operates using a body with a jaw component, actuated by two lever arms. An initial movement of the lever arms grips the pin to be removed and continued movement of the lever arms causes the pin to be displaced from the substrate. The pin is gripped by entering the jaw component through an aperture in the nose of the tool, then the pin must extend through the jaw component and out the other side in order to be effectively gripped by the opposing forces at each end of the jaw. This limits the use of the tool to extraction of pins that are long enough to extend through the jaw component, as shorter pins that are unable to reach through the jaw component are unable to be adequately held with any force.

In addition, removal tools such as those disclosed above contain a number of different components and working parts in order for the tool to operate. Instruments of multiple parts are less desirable in a surgical environment, as they are more difficult to clean and have an increased likelihood of one or more parts breaking or not performing properly, affecting the ability to use the entire tool.

OBJECT OF THE INVENTION

It is an object of the invention to provide a gripping tool for use in pin extraction that overcomes the disadvantages described above.

Alternatively, it is an object of the invention to at least provide the public with a useful choice.

SUMMARY OF THE INVENTION

According to a first aspect of the invention, there is provided a gripping tool for extracting a pin during a surgical procedure, the gripping tool including:

two lever arms, each arm having a nose end and a handle end, the two lever arms joined together proximate to but spaced apart from the nose end by a bridging portion, the bridging portion including a central fulcrum region;

the nose ends of each the lever arms having one or more teeth adapted to interlock with the one or more teeth of the other lever arm;

each nose end having a longitudinal aperture therein extending through the interlockable teeth adapted, in use, to align and receive the pin;

such that in use, urging together the handle ends of the lever arms causes the nose ends to move relative to each other such that the interlockable teeth misalign and grip the pin.

In preferred embodiments of the invention each lever arm includes a plurality of teeth. More preferably, each lever arm includes two teeth.

Preferably, the nose ends of the lever arms and bridging portion are integrally formed as a single piece. More preferably, the gripping tool is integrally formed as a single piece.

Preferably, the bridging portion includes a flexure hinge.

Preferably, the bridging portion includes an aperture extending through the bridging portion, the aperture adapted, in use, to align and receive the pin.

In further preferred embodiments the bridging portion and one or more interlockable teeth are spaced apart from each other. More preferably the bridging portion and one or more interlockable teeth are separated by one or more cavities.

Preferably, the one or more interlockable teeth of a first lever arm and the one or more interlockable teeth of the opposing lever arm are dimensioned to create a gap therebetween.

More preferably, the interlockable teeth are dimensioned to create a serpentine shaped gap therebetween.

Preferably, the nose and handle ends of each lever arm are on the same side of the longitudinal axis of the gripping tool.

In preferred embodiments of the invention urging together of the handle ends of the lever arms causes the interlocking teeth to move apart.

Preferably, one or more of the lever arms include one or more means to limit the amount the lever arms can be moved together about the fulcrum region.

More preferably, the means for limiting comprises one or more projections on each lever arm, each projection adapted to, in use, contact an opposing projection on the opposite lever arm, in order to limit the amount the lever arms can be moved about the fulcrum region.

In one preferred embodiment, the means for limiting comprises two projections on each lever arm in the form of opposing flanges, wherein the flanges are located proximate the bridging portion.

Even more preferably, the two flanges define a recess therebetween on each lever arm.

In further preferred embodiments the outer plane of each flange is inset from the outer surface of the lever arm on which the flange is located.

Preferably, opposing surfaces of each flange are outwardly curved.

In a further alternative preferred embodiment, the means for limiting comprises a first projection extending from a first lever arm proximate the bridging portion and a second projection extending from a second lever arm, the second projection adjacent and adapted to be interlockable with the first projection, the first and second protrusions dimensioned to create a gap therebetween.

More preferably, the first and second protrusions are dimensioned to create a serpentine shaped gap therebetween.

In further preferred embodiment the one or more lever arms include protrusions or indentations proximate the handle end of the lever arm.

In further embodiments of the invention the tool includes a nail removal means proximate the handle end of one or both lever arms.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

A preferred embodiment of the gripping tool of the present invention can by described in more detail with reference to FIGS. 1 to 8.

The tool of the present invention is suitable for use in the removal of pins or other elongate members from a substrate, in particular for the use of removing surgical pins during a surgical procedure. This is not intended to be limiting and it is envisaged the tool of the present invention may be utilised across a range of fields where gripping and extraction of elongate members, particularly short ones, may be required.

Figure 1:
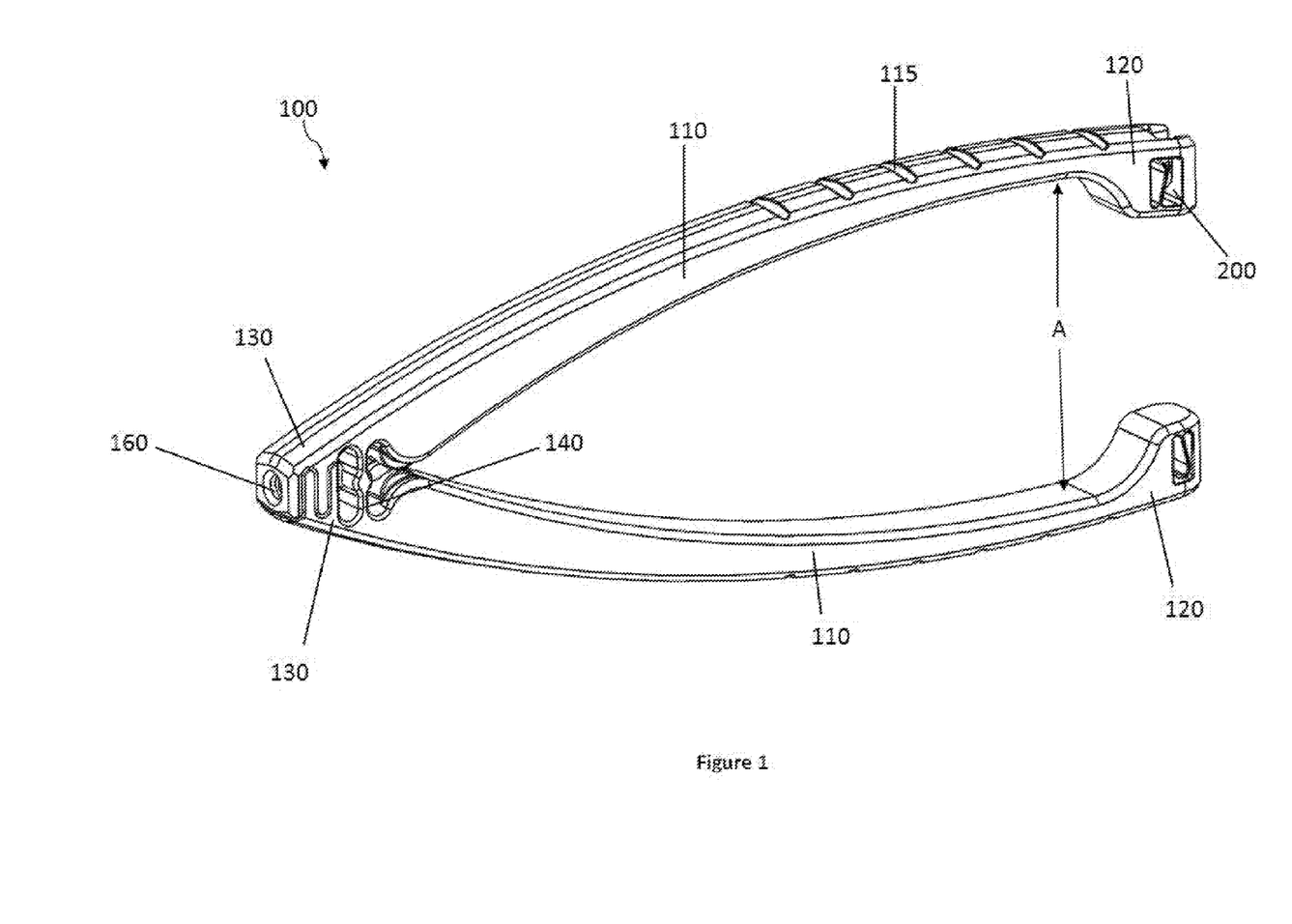
FIG. 1 shows a front perspective view of the gripping tool in a preferred embodiment of the invention.

FIG. 1 shows a perspective view of gripping tool 100 including lever arms 110, each having a handle end 120 and a nose end 130. In the preferred embodiment shown in the Figures, lever arms 110 are substantially arcuate or partially arcuate along the length, with a substantially quadrilateral cross section across the width. Lever arms 110 may also include ergonomic features such as bevelled edges and protrusions of indents 115 position at one or more places along lever arm 110 to aid the user in firmly grasping the tool without risk of slipping. When not in use, handle ends 120 are spaced apart by a distance A, allowing space for the urging together of lever handle ends 120 when tool 100 is in use. Distance A may vary depending on the form of lever arms 110 taken.

Lever arms 110 may also take other forms not shown in FIG. 1, such as lever arms with circular, oval or triangular cross sections, lever arms with one or more bends along the length of one or more of the lever arms, or lever arms with a varying cross section across the width at different points along the length of the lever arms. The arcuate shape of the lever arms in the preferred embodiment is not intended to be limiting and lever arms 110 may be formed substantially straight, or with the obtuse angle being greater or small than that shown in FIG. 1 depending on the size of the tool or its specific use. The length of lever arms 110 may also vary as needed, for example a pin needing extracting that is located in a deep or space restricted location may require a longer tool than that designed to extract pins from an unobstructed flat surface. In preferred embodiments of the current invention, lever arms 110 and consequently tool 100 is between 120 mm-160 mm in length, more preferably 140-150 mm in length.

Figure 3:
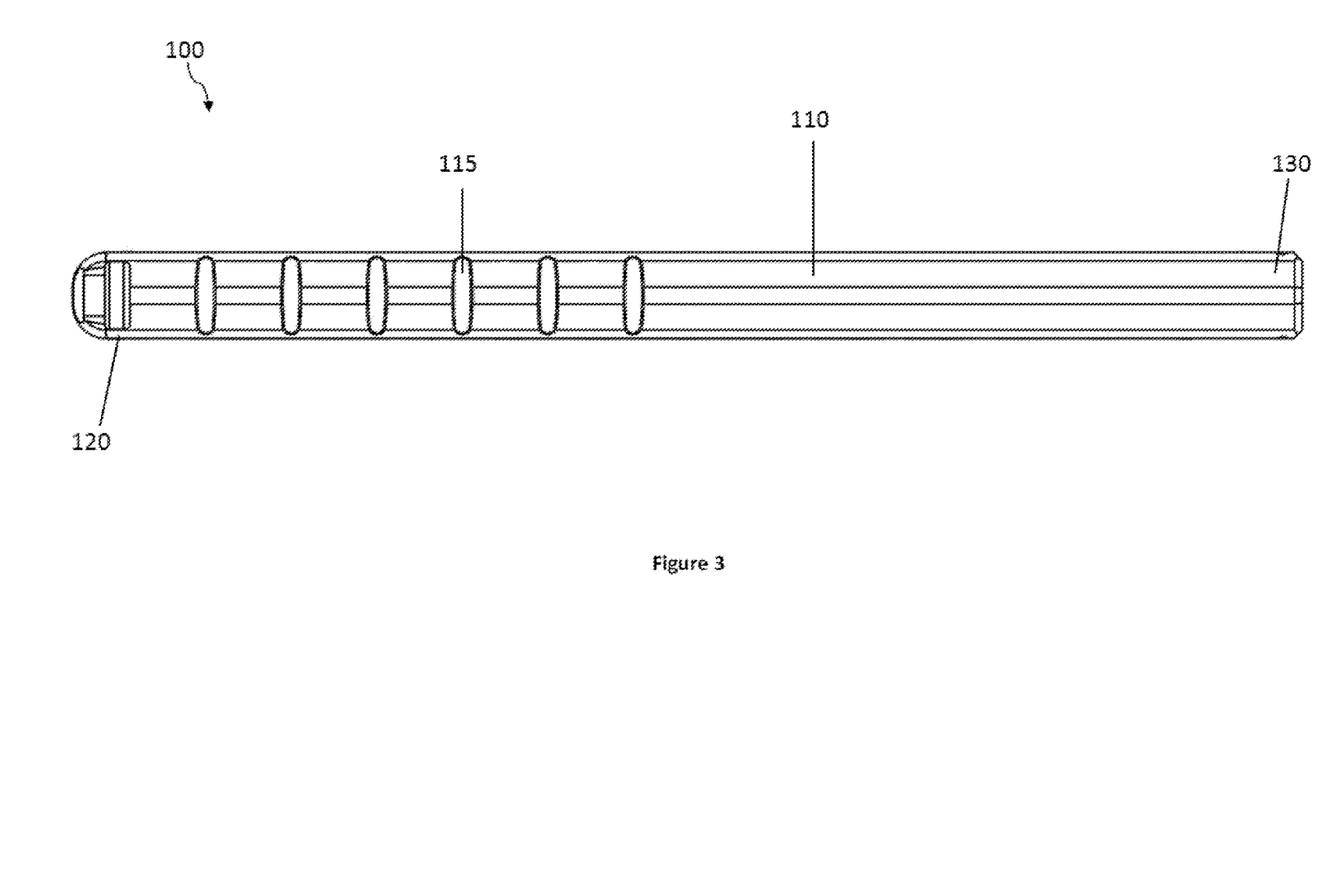
FIG. 3 shows a top view of the gripping tool shown in FIGS. 1 and 2.

In preferred embodiments handle ends 120 of lever arms 110 are enlarged and protrude inwardly towards the opposing lever arm 110. Such enlargement allows for the inclusion of optional additional tooling means such as nail removal tool 200, discussed in more detail below, to be included at the end of one or both of lever arms 110. In other embodiments handle ends 120 of lever arms 110 may include or be formed with features such as rings, hooks, apertures or protrusions of varying shapes in order to allow the tool to be suitable for use with additional tasks, or for easy of storage, handling or cleaning. FIG. 3 shows a top view of the side of gripping tool 100 and indicates indents 115 and nail removal tool 200 located proximate to handle end 120 of lever arm 110 and extending approximately up to halfway along lever arms 110. In other embodiments indents 115 or protrusions may be positioned at any location as needed to provide an effective non-slip surface to the user as determined in part by the size and shape of the lever arms.

When not in use, lever arms 110 are connected at bridging portion 140 located proximate to nose end 130. Nose end 130 of tool 100 is shown in more detail in FIGS. 4, 5, 6 and 7. Bridging portion 140 is preferably formed of the same resilient material as the lever arms and includes two substantially opposing surfaces separated by a dimension B narrow enough to allow bridging portion 140 to act as a flexure hinge having a fulcrum 145. Bridging portion 140 is preferably the same width C as lever arms 110, the outwardly facing surfaces of bridging portion 140 being substantially flush with the outer surfaces of lever arms 110.

Bridging portion 140 is preferably formed with arcuate ridges 146 extending from the opposing faces of the bridging portion, the arcuate ridges running substantially the width C of bridging portion 140. Ridges 146 increase strength at fulcrum 145, which acts as a flexure hinge when tool 100 is in use and lever arms 110 are urged together in direction X. Strengthening of fulcrum 145 may be achieved by reinforced regions taking other forms such as curved or squared shapes for example and bridging portion 140 may also may contain grooves or protrusions at varying positions to aid in flexing or reinforcement of bridging portion 140.

Figure 6:
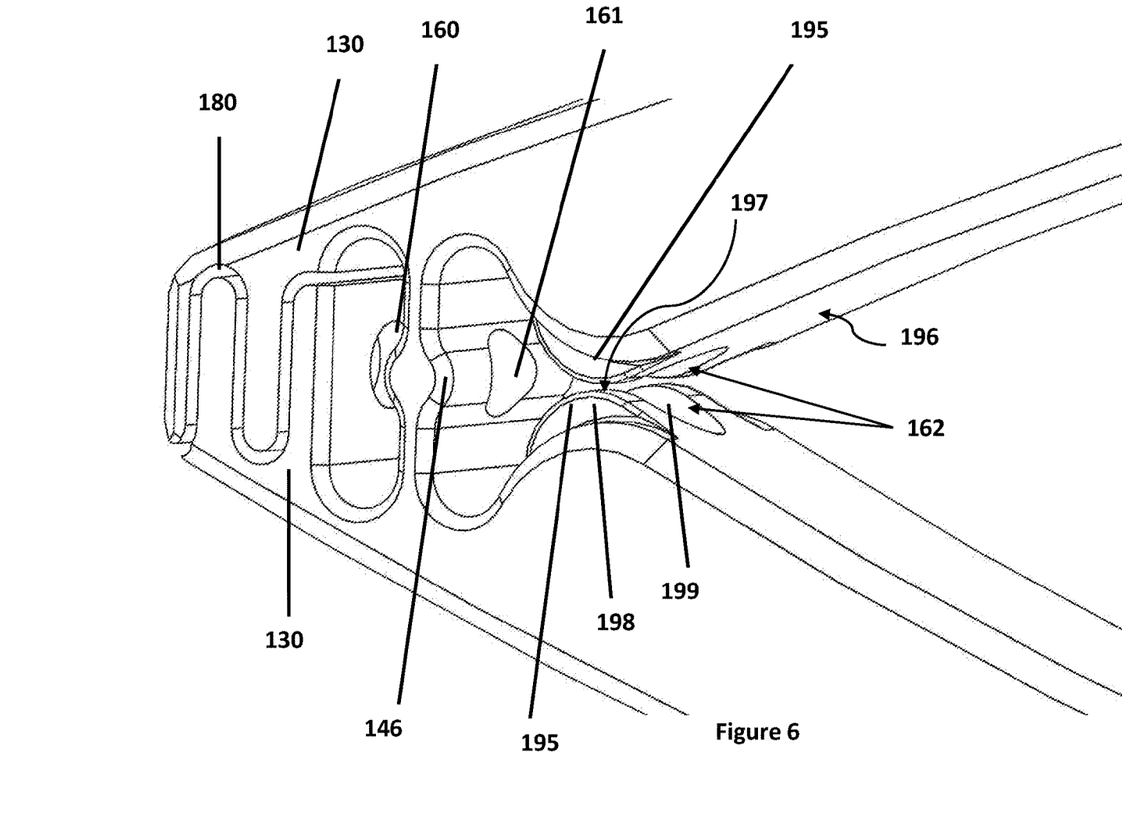
FIG. 6 shows a perspective view of the nose portion of the gripping tool as shown in FIGS. 1 to 5.

In preferred embodiments, bridging portion 140 includes an aperture 161 as can be seen in more detail in FIG. 6. Aperture 161 is formed substantially in the centre of width C of arcuate ridges 146 and extends from the arcuate ridge 146 on one face of the bridging portion through the bridging portion to the arcuate ridge 146 on the opposing face of the bridging portion. Aperture 161 is positioned to align with further apertures 160 that are formed in teeth 170-173 and recess 162 formed between limiting means 195 as described in more detail below. Aperture 161 is dimensioned such that it has a diameter large enough to receive pins of varying dimensions, but not so large that the aperture reduces the strength of the bridging portion to a level where it yields, plastically deforms or fails, causing damage to the tool. The size of such an aperture will be apparent to those familiar in the art and with the range of pins and pin sizes used in surgical procedures.

Bridging portion 140 may be formed with other hinge mechanisms such as a living hinge or a conventional hinged pivot. The most preferable hinges are those that are able to accommodate aperture 161 and do not result in increased bulk or multiple working components to tool 100. As such, a flexure hinge having fulcrum 145 as shown in the Figures is the most preferred embodiment due to its single piece construction and streamlined dimensions, but is not intended to be limiting.

Figure 4:
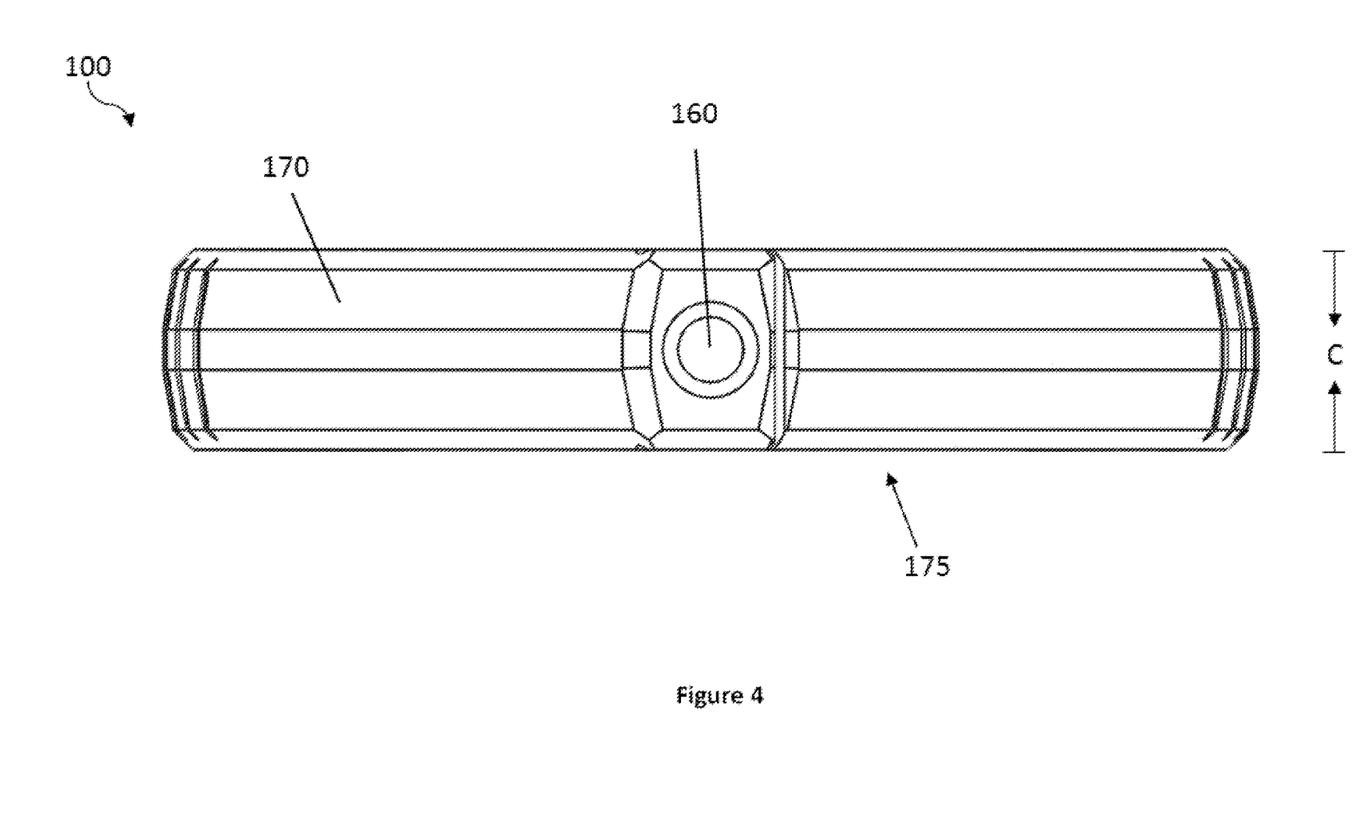
FIG. 4 shows an end view of the nose portion of the gripping tool of FIGS. 1 to 3.
Figure 5:
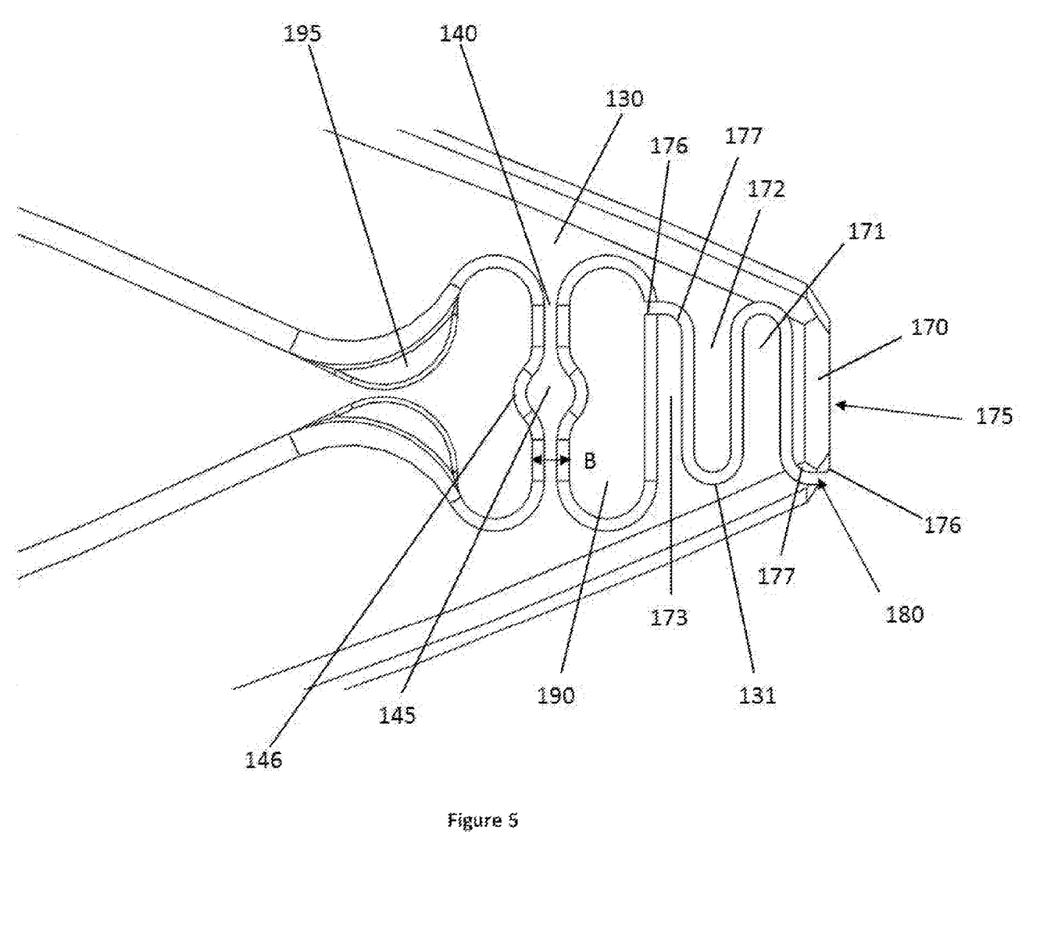
FIG. 5 shows a side view of a first side of the nose portion of the gripping tool as shown in FIGS. 1 to 4.

In the preferred embodiment shown in FIGS. 4, 5 and 6, nose ends 130 of lever arms 110 are formed with two teeth 170 and 172, or 171 and 173 extending inwardly from inner wall 131 of the lever arm so as to interlock with two opposing teeth 170 and 172, or 171 and 173 on the nose end of opposing lever arm 130. Teeth 170-173 are preferably formed as flanges with two opposing planar faces extending the width C of tool 100, the outer surfaces of teeth 170-173 being substantially flush with the outer surfaces of lever arms 110. Teeth 170-173 extend from each lever arm 130 towards opposing lever arm 130 and are dimensioned to extend towards the opposing lever arm such that a gap 180 is created between opposing teeth 170-173.

Gap 180 extends between a first tooth 170 that forms the front face 175 of tool 100, between opposing second 171 and third teeth 172 and fourth tooth 173 into cavity 190, creating a serpentine shaped gap between each lever arm at nose ends 130, where the preferred gap size is substantially 0.45 mm. Cavity 190 has a substantially peanut-spectacle shape the walls of cavity 190 formed from the connection between sides of bridging portion 140 and fourth tooth 173.

Cavity 190 provides space for a pin to extend into, allowing the user to perform a number of "grips" and extractions on a single pin as it is extracted from a substrate. In addition, cavity 190 adds length to the nose end of tool 100, as may be required for different uses. The shape of size of cavity 190 may be changed in order to produce a tool with a longer or shorter nose portion, depending on the requirements of the user. However, it should be appreciated that the relative proximity of bridging portion 140 to teeth 170-173 in comparison to the distance between bridging portion 140 and handle ends 120 of lever arms, provides a mechanical advantage for increasing the grip force that can be applied at the nose end of the tool 100. Cavity 190 should therefore not be formed to such an extent that this mechanical advantage is lost.

As seen most clearly in FIG. 5, teeth 170 and 173 are formed as flanges with the ends of the flanges distal from lever arm from which it extends having a substantially square corner edge 176 and a substantially rounded corner edge 177, the planar face 175 and square corner edge 176 of tooth 170 forming the nose face of tool 100, and the planar face and square corner edge 176 of tooth 173 forming part of the wall of cavity 190.

As would be clear to a person skilled in the art, while it is preferably that four teeth are used in the current invention, different numbers of teeth may be used in tool 100. More than four teeth may be used in a tool with a longer nose portion that can remove larger pins for example, or alternatively each lever arm may be formed with a single tooth.

Teeth 170-173 further include an aperture 160 extending through each of teeth 170-173 as can be seen most clearly in FIGS. 4 and 6. Aperture 160 is formed as a longitudinal hole centrally aligned on nose face 175 of tooth 170 and extends in direct alignment though interlocked teeth 171, 172 and 173. The shape of the aperture is preferably cylindrical, allowing for a pin to be received within aperture 160, the pin being able to extend through each of teeth 170-173 into cavity 190. The size of the aperture may vary depending on the type of pins it is designed to receive, however size of aperture 160 should not be so large that it weakens the teeth and consequently is less effective in gripping an object under force.

Teeth 170-173 are preferably of a length such that aperture 160 is not formed at or near the end of each tooth distal from the lever arm 130 to which it extends. Teeth 170-173 are formed, as seen in FIG. 6, to extend from lever arm 130 such that aperture 160 is fully enclosed by each of the teeth, strengthening the aperture and consequently increasing the amount of force capable of being placed on the teeth without risk of failure. This configuration also allows for nose ends of lever arms 130 to move away from each other to grip the pin. In addition this configuration also allows for nose ends of lever arms 130 to also grip a pin should they be squeezed together as opposed to pulled apart.

In alternative embodiments not shown, teeth may extend up to an aperture but no further, forming teeth with grooved or recessed end faces. This embodiment may be used when tool 100 is designed such that teeth 170-173 are forced together to grip a pin, rather than forced apart.

Aperture 160 may include bevelled edges at the entrance to the aperture at face 175, or may include additional grooves or smoothed edges to facilitate guiding a pin to be gripped and extracted into the aperture. This can be particularly difficult during a surgical procedure when visibility is reduced.

In alternative embodiments (not shown) a groove or hollow portion may extend from the opening of aperture 160 at front face 175 of tooth 170 to the outer wall of one or both lever arms, providing a guidance path for a pin to travel along before entering aperture 160. Such guidance path may aid in locating pins in situations of particularly difficult access.

Tool 100 further includes a means for limiting the amount the lever arms can be moved together about the fulcrum 145. As seen in FIGS. 5 and 6, the means for limiting movement of the lever arms comprises flanges 195, each lever arm 110 providing two flanges 195 located on the inner surface 196 of each lever arm 110, proximate the bridging portion 140 and near the handle side of fulcrum 145.

Each pair of flanges 195 are positioned to directly oppose the flanges on the other lever arm, and are preferably in the form of curved walls having an outwardly curved upper surface 197, the upper surface 197 supported by two substantially planar opposing walls 198 extending from the surface 196 of lever arms 110 to curved upper surface 197.

Each pair of flanges 195 on each lever arm are spaced apart, defining a recess 162 therebetween on each lever arm. Recess 162 is formed by the inner walls 199 of flanges 195 and runs the length thereof, the width of the recess substantially corresponding to the diameter of aperture 161 in bridging portion 140.

Flanges 195 are preferably spaced apart such that recess 162 is aligned with aperture 161, allowing for a pin to extend through aperture 161 into recess 162 without bending the pin.

The flanges as shown in the preferred embodiments are not intended to be limiting, and flanges or protrusions of other shapes may be utilised to limit the amount the lever arms can move around the fulcrum 145. In alternative embodiments the flanges 195 may not define the recess 162 and recess 162 may be formed by a depression or groove in lever arm 110 for example.

Figure 7:
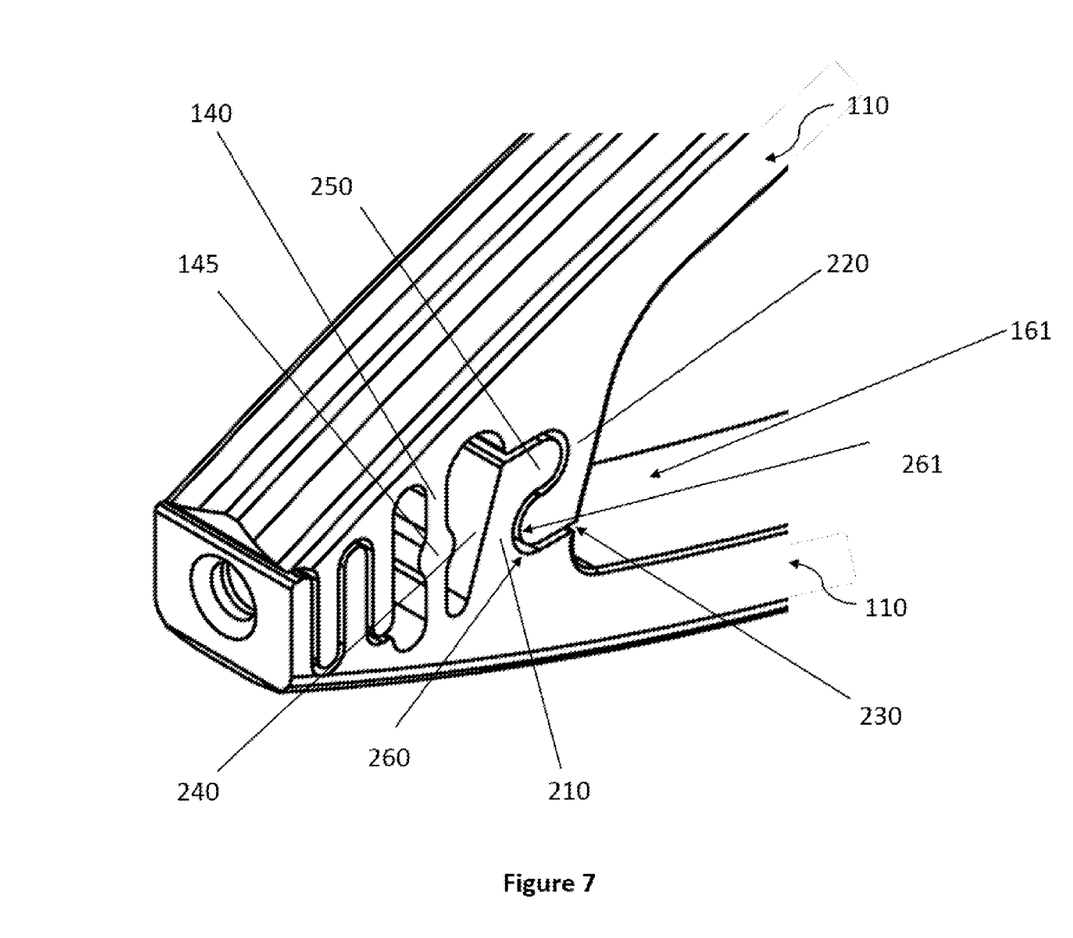
FIG. 7 shows a perspective view of the nose portion of the gripping tool in an alternative embodiment of the invention.
Figure 8:
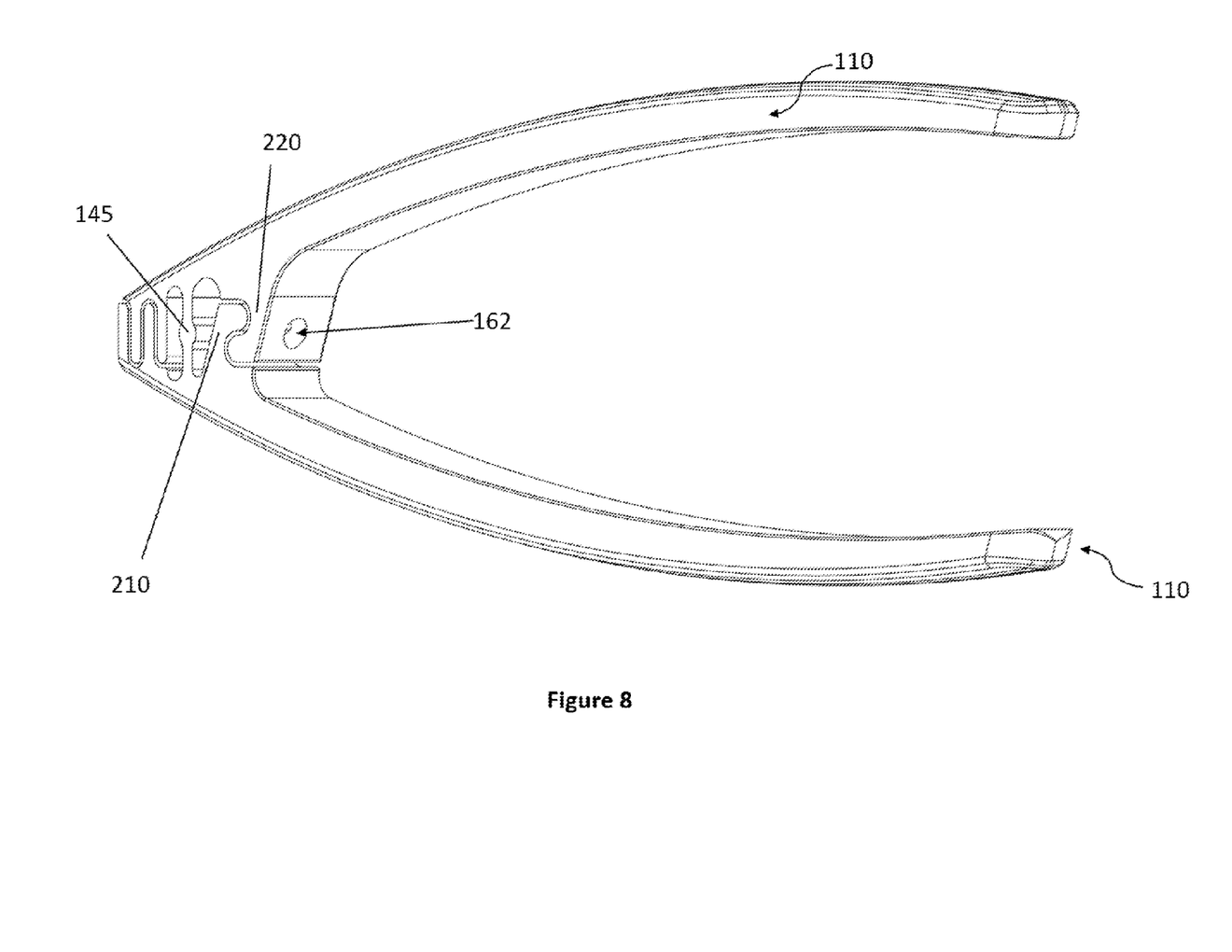
FIG. 8 shows a rear perspective view of the tool of FIG. 7.

An alternative example of a means for limiting the amount the lever arms can move around the fulcrum 145 can be seen in FIG. 7 and FIG. 8. In this embodiment the limiting means are in the form of first projection 210 and second projection 220 which extend inwardly from lever arms 110. Projections 210 and 220 are each shaped to include a substantially planar first edge 240 and a curved nose portion 250, forming projections having serpentine shaped outer surfaces 260 and 261. Projection 220 is substantially a mirror image of projection 220, allowing the two projections to interlock together at surfaces 260 and 261 when tool 100 is in use.

In the preferred embodiment shown in FIGS. 7 and 8 projections 210 and 220 are dimensioned such that when not in use, they define a gap 230 therebetween, defined by surfaces 260 and 261, in a similar fashion to teeth 170-171 as seen in FIG. 5. In the preferred embodiment shown, gap 230 is serpentine shaped and preferably 0.3-2.0 mm wide, and more preferably 0.4-0.6 mm wide. Gap 230 is dimensioned such that it is large enough to allow sufficient movement of the lever arms 110 to allow for adequate gripping by the two sets of opposing teeth 170 and 172, and/or 171 and 173. Equally, gap 230 is dimensioned such that it is small enough to prevent over stressing of the bridging portion 145 which would otherwise result in yielding, plastic deformation or failure as mentioned above.

Apertures 161 extends through bridging portion 140 to aperture 162, which extends through each of projections 210 and 220 as seen in FIG. 8, allowing for a longer pin to be retained within the tool, or for a shorter pin to move into as it is removed from a substrate.

In use, when lever arms 110 are forced together in direction X (see FIG. 2) surface 260 and 261 abut as projections 210 and 220 are forced together, limiting the range of movement of levers 110 in direction X to the width of gap 230.

Projection 210 and 220 may also act as further gripping means when a pin of sufficient length is inserted through apertures 160-162, with projections 210 and 220 gripping a pin in a similar way to teeth 170-173 as described earlier.

Figure 2:
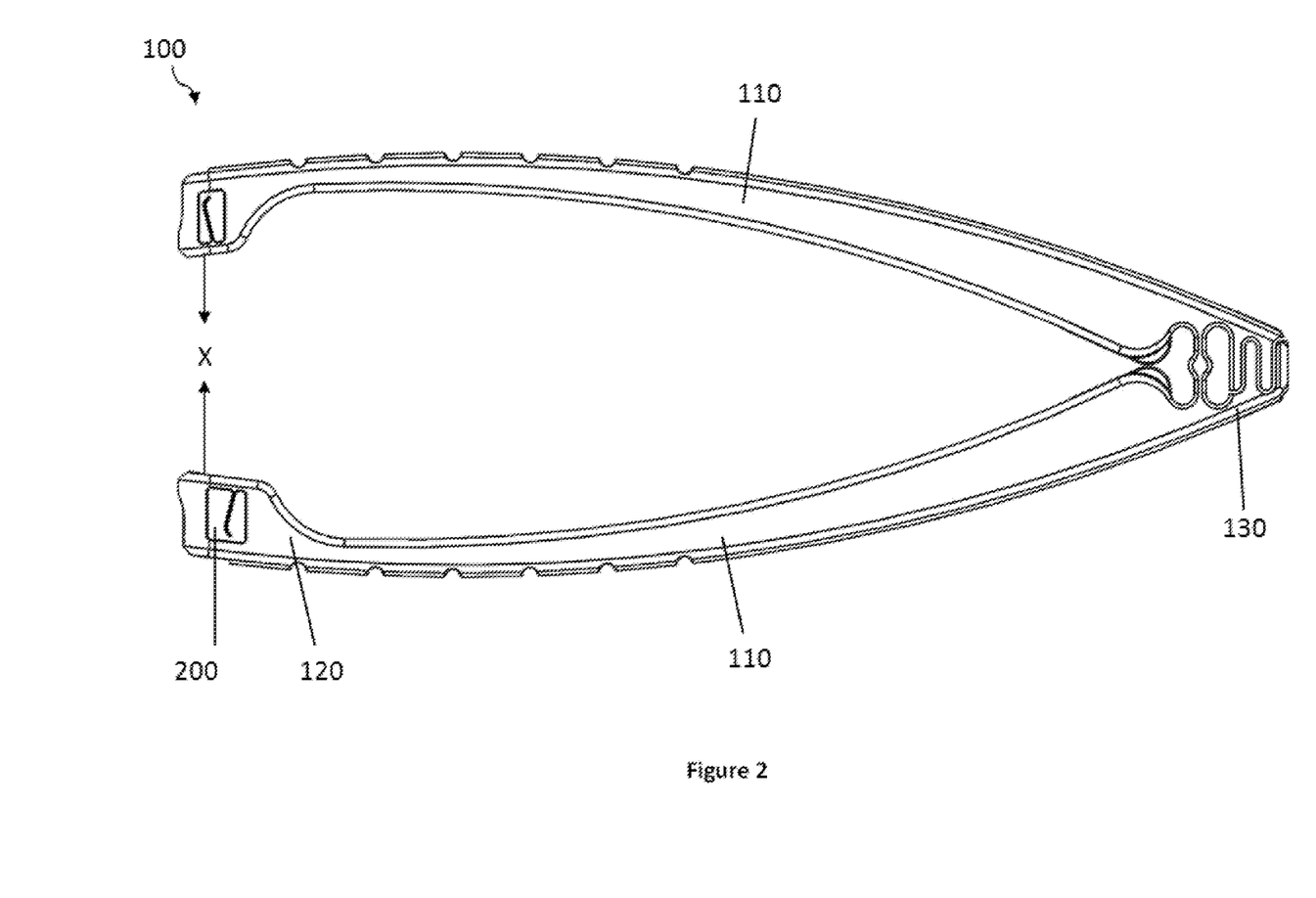
FIG. 2 shows a side view of the gripping tool of FIG. 1.

Tool 100 may include additional tooling components, preferably located at or near the handle ends 120 of lever arm or arms 110. As seen in FIGS. 1, 2 and 3, in one embodiment tool 100 includes a nail removal means 200. Nail removal means 200 may be formed using any number of mechanisms known in the art that are suitable to incorporation into the handle portion of a lever arm, without compromising any of the advantages provided by the tool itself.

The tool 100 of the present invention is preferably manufactured as an integrally formed unit. Lever arms 110 are integrally connected via bridging portion 140 such that entire tool 100 is formed as a single piece construction. This has a number of distinct advantages, most particularly being that the single piece construction makes the tool significantly easier to clean in comparison to similar tools formed from multiple working parts. The tool itself is less complex and therefore has a reduced risk of failure associated with tools having individual parts that make up the main instrument.

In alternative embodiments, the tool of the present invention may be formed from two or more parts, for example bridging portion 140 may centrally connect two individual lever arm portions using a screw or pivot mechanism or other hinge mechanism.

In use, a pin or other elongate member may be gripped and pulled or extracted from a substrate by tool 100. For the purposes of describing the tool in use, the removal of a headless pin during a surgical operation will be discussed without intended limitation.

Typically pins removed during a surgical procedure will have a very small length of pin extending from a substrate (typically bone or cutting guide) that is available to be gripped, with the preferred tool of the present invention designed to remove pins having a minimum of approximately 2-3 mm of pin length available to form a grip on. Pins of shorter lengths may be extracted more effectively using a tool of the current invention having teeth with narrower widths as would be understood by a skilled person.

Aperture 161 located in bridging portion 140 and recess 162 located between limiting means 195 ensure there is no maximum pin length limit, as any extending pin length is guided by aperture 161 and recess 162 to extend between handle ends of lever arms 120 and further if necessary.

In alternative tools of the present invention designed specifically to extract very short pins, the tool may be designed with narrow teeth, and may also not include aperture 161 through bridging portion 140 or recess 162, which are designed to accommodate longer pin lengths.

Once a pin to be extracted has been identified, the surgeon grips tool 100 in a single hand by lever arms 110 at the handle end 120. The nose of the tool is directed towards the pin, with front face 175 being placed over the pin such that the pin enters longitudinal aperture 160. Tool 100 may then be pushed down onto the pin further by the user to ensure the maximum length of pin is inserted within apertures 160-162 as possible. Preferably, the pin will extend through the aperture 160 in teeth 170, 171, 172 and 173 through cavity 190, and if the pin is of sufficient length, through corresponding apertures 161 in bridging portion 140 and recess 162 between limiting means 195, providing the opportunity for maximum grip. However, if a pin length is not long enough to reach through the nose portion entirely, the pin may span only the first gap 180 between teeth 170 and 171 in order to be effectively gripped by tool 100. As would be clear to a person skilled in the art, the further into aperture 160 the pin can be inserted, the stronger grip the tool can achieve on the pin.

As mentioned above, a surgeon may use the bevelled entrance to aperture 160 to help slide or guide the pin into the correct position.

Once the tool is in the correct position lever arms 110 are urged together by the user in direction X as shown in FIG. 2. As lever arms 110 are forced together, bridging portion 140 flexes at fulcrum 145, forcing the nose end of lever arms 130, and consequently interlocking teeth 170-173 apart from each other, misaligning the longitudinal aperture 160 running through each of teeth 170-173. When a pin has been received within aperture 160 and lever arms 110 are urged together, the pin is firmly gripping in position by the opposing forces caused by the misalignment of teeth 170-173. As teeth 170 and 172 are forced away from teeth 171 and 173, the opposing forces acting on the pin firmly hold the pin in position within aperture 160.

As lever arms 110 are urged together at handle end 120, arcuate ridges 146 around fulcrum 145 provide an increased cross-section of the flexure hinge immediately adjacent aperture 161, resulting in an increased uniformity of deformation over the entire width C as bringing portion 140 bends around fulcrum 145.

Once the pin has been gripped, the user pulls tool 100 away from where the pin has been held, while maintaining the urging grip on lever arms 110. The pin is removed from the substrate, then can be released from teeth 170-173 by releasing the grip on lever arms 110. As the grip on the lever arms is released, teeth 170-173 return to a resting position, aligning aperture 160 through each of the teeth, thereby releasing the pin.

As a pin is extracted from a substrate it may be gripped and pulled a number of times before it is fully extracted. With each extraction the pin extends further from the substrate and extends further through teeth 170-173. As pin length increases, the body of the pin is received within aperture 161 in bridging portion 140 and recess 162 located between flanges 195. Both aperture 161 and recess 162 act to maintain a straight pin alignment, making extraction easier and decreasing the risk of the pin snapping or bending accidentally as it is withdrawn. This alignment means is useful for both pins that have increased length as they are extracted and those that have a significant length to begin with. For pins that are long enough to extend through apertures 160, 161 and recess 162 prior to extraction, the user ensures the pin is correctly placed and aligned through each of these guiding features before extraction begins.

Flanges 195 prevent the surgeon from being able to exert too much force when urging lever arm handles 120 together, as opposing flanges 195 contact each other as levers 120 are urged together and prevent the lever arms from moving any closer together. These flanges prevent over travel that may damage a pin being gripped and also prevent damage to the instrument itself that may be caused by excessive flexing of bridging portion 140. Excessive flexing may result in yield of the flexure hinge and may cause permanent damage to tool 100.

The outer plane 198 of each flange 195 is inset from the outer surface of the lever arms 110. In use, this inset positioning helps to remove any potential pinch points that could cause a surgeon to pinch any tissue, gloves or fingers for example between the lever arms accidentally.

Tool 100 as shown in FIGS. 1 to 6 is designed in the preferable configuration wherein lever arms 110, and corresponding lever arm nose end 130 and handle end 120 are on the same side of a longitudinal axis running from the nose end of tool 100, through the fulcrum 145 to the handle ends 120 of each lever arm.

In alternative embodiments, the nose end 130 of each lever arm 110 may be on the opposite side this longitudinal axis to handle end 120, creating a crossing of the two lever arms at fulcrum 145. In this embodiment, urging together of lever arms at the handle end will force the opposing teeth together instead of apart, resulting in a misalignment of aperture 160 and a gripping of an inserted pin. The direction of misalignment in the alternative embodiment is opposite to that of the embodiment disclosed herein, however is still equally effective provided the gap 180 is of a size that will allow nose ends 130 of lever arms 110 to be compressed together to create the misalignment, as would be clear to a person skilled in the art.

The tool 100 of the present invention is preferably formed from a surgical grade stainless steel, however this is not intended to be limiting. The tool of the present invention may be formed from any material that has elastic deformation properties as well as sufficient hardness and strength to withstand applied loads required for pin extraction.

The tool 100 of the present invention has number of advantages over the prior art. The single piece construction and absence of multiple moveable parts provides a sturdy tool that is easily cleaned and sterilised in a medical or other environments requiring sterile conditions.

The lack of separate parts that may break or become disconnected or misaligned reduces time spent and money wasted when instruments are broken, or need to be taken apart and reassembled before being used again.

The use of multiple interconnecting teeth to securely grip a very small pin of, for example, 3 mm provides significant advantages over known prior art tools that require a longer pin before the pin can be successfully gripping and extracted from a substrate. Often pins in surgical procedures are pushed in too far and need to be extracted, and without a tool that can grip a pin very close to the nose end of the tool, such pins are often unable to be removed, as the gripping means is located too far into the nose of the extraction tool. Pins of lengths less than 5 mm are very difficult to remove using currently available instruments, resulting in increased time in surgery for the patient. The tool of the current invention addresses this problem, resulting in surgical procedures being completed in a shorter timeframe and consequently, better patient outcomes.

The tool of the present invention has been described in a preferred embodiment above and it should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

The invention claimed is:

1. A gripping tool for extracting a pin during a surgical procedure, the gripping tool including:
   two lever arms, each arm having a nose end and a handle end, the two lever arms joined together proximate to but spaced apart from the nose end by a bridging portion, the bridging portion including a central fulcrum region;
   the nose ends of each the lever arms having one or more teeth adapted to interlock with the one or more teeth of the other lever arm;
   each nose end having a longitudinal aperture therein extending through the interlocking teeth adapted, in use, to align and receive the pin, wherein the longitudinal aperture is aligned with a longitudinal axis of the gripping tool centrally aligned between the lever arms and running from the nose ends to the handle ends of the lever arms;
   such that in use, urging together the handle ends of the lever arms causes the nose ends to move relative to each other such that the interlocking teeth misalign and grip the pin.

2. The gripping tool of claim 1, wherein each lever arm includes a plurality of teeth.

3. The gripping tool of claim 1, wherein the nose ends of the lever arms and bridging portion are integrally formed as a single piece.

4. The gripping tool of claim 1, wherein the bridging portion includes a flexure hinge.

5. The gripping tool of claim 1, wherein the bridging portion includes an aperture extending through the bridging portion, the aperture adapted, in use, to align and receive the pin.

6. The gripping tool of claim 1, wherein the bridging portion and one or more interlocking teeth are spaced apart from each other.

7. The gripping tool of claim 6, wherein the bridging portion and one or more interlocking teeth are separated by one or more cavities.

8. The gripping tool of claim 1, wherein the one or more interlocking teeth of a first lever arm and the one or more interlocking teeth of the opposing lever arm are dimensioned to create a gap therebetween.

9. The gripping tool of claim 8, wherein the interlocking teeth are dimensioned to create a serpentine shaped gap therebetween.

10. The gripping tool of claim 1, wherein the nose and handle ends of each lever arm are on the same side of the longitudinal axis of the gripping tool.

11. The gripping tool of claim 1, wherein one or more of the lever arms include one or more means to limit the amount the lever arms can be moved together about the fulcrum region.

12. The gripping tool of claim 11, wherein the means for limiting comprises one or more projections on each lever arm, each projection adapted to, in use, contact an opposing projection on the opposite lever arm, in order to limit the amount the lever arms can be moved about the fulcrum region.

13. The gripping tool of claim 12, wherein the means for limiting comprises two projections on each lever arm in the form of opposing flanges, wherein the flanges are located proximate the bridging portion.

14. The gripping tool of claim 13, wherein the two flanges define a recess therebetween on each lever arm.

15. The gripping tool of claim 14, wherein an outer plane of each flange is inset from an outer surface of the lever arm on which the flange is located.

16. The gripping tool of claim 15, wherein an opposing surfaces of each flange are outwardly curved.

17. The gripping tool of claim 12, wherein the means for limiting comprises a first projection extending from a first lever arm proximate the bridging portion and a second projection extending from a second lever arm, the second projection adjacent and adapted to be interlockable with the first projection, the first and second projections dimensioned to create a gap therebetween.

18. The gripping tool of claim 17, wherein the first and second projections are dimensioned to create a serpentine shaped gap therebetween.

19. The gripping tool of claim 1, wherein the tool includes a nail removal means proximate the handle end of one or both lever arms.

* * * * *

UNITED STATES PATENT AND TRADEMARK OFFICE
CERTIFICATE OF CORRECTION

PATENT NO. : 10,099,358 B2  
APPLICATION NO. : 15/004482  
DATED : October 16, 2018  
INVENTOR(S) : Iain Alexander McMillan and Simon John Faichen Davis Page 1 of 1

It is certified that error appears in the above-identified patent and that said Letters Patent is hereby corrected as shown below:

On the Title Page

After (22) Filed: January 22, 2016, add:
"(30) Foreign Application Priority Data: January 23, 2015 (NZ) 704136"

Signed and Sealed this
Fourteenth Day of January, 2020

Andrei Iancu
*Director of the United States Patent and Trademark Office*